United States Patent
Canuto

(10) Patent No.: US 11,377,370 B2
(45) Date of Patent: Jul. 5, 2022

(54) WATER TURBINE THAT CAPTURES IONIC SURFACTANTS OF THE WATER FROM POLLUTED RIVERS AND SEAS USING MANTLE PERIODOTITE CARBON MINERALIZATION BASED ACTIVATED CARBON FOR PURIFICATION

(71) Applicant: Teresita Amponin Canuto, Van Nuys, CA (US)

(72) Inventor: Teresita Amponin Canuto, Van Nuys, CA (US)

(*) Notice: Subject to any disclaimer, the term of this patent is extended or adjusted under 35 U.S.C. 154(b) by 0 days.

(21) Appl. No.: 16/873,801

(22) Filed: Jul. 13, 2020

(65) Prior Publication Data

US 2022/0009796 A1    Jan. 13, 2022

(51) Int. Cl.
| | | |
|---|---|---|
| *C02F 1/28* | (2006.01) | |
| *A61K 31/105* | (2006.01) | |
| *C01B 33/22* | (2006.01) | |
| *B01J 20/20* | (2006.01) | |
| *C02F 103/08* | (2006.01) | |
| *C02F 103/00* | (2006.01) | |

(52) U.S. Cl.
CPC ............ *C02F 1/283* (2013.01); *A61K 31/105* (2013.01); *B01J 20/20* (2013.01); *C01B 33/22* (2013.01); *C02F 2103/007* (2013.01); *C02F 2103/08* (2013.01); *C02F 2201/001* (2013.01)

(58) Field of Classification Search
CPC ...... C02F 1/28; C02F 1/283; C02F 2103/007; C02F 2103/08; C02F 2201/001; A61K 31/105; B01J 20/20; C01B 33/22
USPC .......................................................... 423/331
See application file for complete search history.

(56) References Cited

U.S. PATENT DOCUMENTS

| | | | | |
|---|---|---|---|---|
| 3,017,347 | A * | 1/1962 | Kratz ...................... | C02F 1/283 210/763 |
| 3,713,542 | A * | 1/1973 | Shaler .................... | C02F 3/046 210/170.1 |
| 5,019,252 | A * | 5/1991 | Kamei ................... | B01D 61/18 210/136 |
| 2010/0133157 | A1 * | 6/2010 | Sun ....................... | C02F 3/1284 210/137 |

* cited by examiner

*Primary Examiner* — Edward M Johnson
(74) *Attorney, Agent, or Firm* — Houda El-Jarrah; Bold IP, PLLC

(57) ABSTRACT

A portable small water turbine with activated carbon water filter is described that has material available to conduct the removal of the ionic surfactants of polluted water from seas and rivers. The portable small water turbine is placed inside a mini boat that is remote controlled. The mini boat (similar to adult/kids RC toy boat) can be dropped-off and picked up from the sea or rivers by a drone. The activated carbon water filter tube contains carbon pads composed of mantle peridotite carbon mineralization based activated carbon.

5 Claims, 5 Drawing Sheets

WATER TURBINE THAT CAPTURES IONIC SURFACTANTS OF THE WATER FROM POLLUTED RIVERS AND SEAS USING MANTLE PERIODOTITE CARBON MINERALIZATION BASED ACTIVATED CARBON FOR PURIFICATION

BACKGROUND OF INVENTION

The present invention relates to removal of the ionic surfactants from the water of polluted rivers and seas caused by environmental pollution. Temperature rise due to effects of rising greenhouse concentrations that affects the global temperature and cause the warming of the planet. Besides using fossil fuels such as oil, coal, and natural gas adds to the atmospheric carbon dioxide ($CO_2$) that warming the planet, environmental pollutants contributed to the rising greenhouse concentration in the atmosphere of the planet. Environmental pollutants that pollute the water of rivers and seas, effect of high level of $CO_2$ in the air ionization of surfactants adsorb in the interfaces, the water-insoluble hydrophobic group may extend out of the water in the air such as methane gas that contributed to the rising greenhouse concentrations that caused the warming of the planet. Sea level rise, ice loss in Greenland and snowmelt in Antarctica.

"Drilodefensin distribution in an earthworm responsible for returning the carbon locked inside the dead plant material back into the ground. Carbon dioxide ($CO_2$): 25×-methane ($CH_4$) i.e. releasing 1 kg. of methane ($CH_4$) in the atmosphere is about equivalent to releasing 298 kg. of $CO_2$. Drilodefensin (hexylethylfuransulfonic acid or HEFS) is the chemical composition." (e.g. Liebelle, Strillmater, et al.)

Six source of atmospheric methane are the following:
1) nature lawn
2) paddy rice fields
3) emission from livestock production system including intrinsic fermentation and animal waste.
4) biomass burning (industrial forest fires, charcoal combustion and firewood).
5) anaerobic decomposition of organic waste in landfills
6) fossil methane emission during the exploration and transport of fossil fuels.

In order to solve the above-mentioned problem, an object of the present invention is to filter the impurities of the water from polluted rivers and seas using water turbine that capture ionic surfactants from the water of polluted rivers and seas that uses mantle peridotite carbon mineralization based activated carbon serves as water purification. The activated carbon filters ionic surfactants, contaminant and impurities of the smallest particle that also kill most bacteria.

Peridotite and ultramafic intrusions (which contain peridotite) are highly reactive rocks from earth's deep interior that is Mg-rich, CA-bearing and is also rich in olivine and pyroxene materials. Using peridotite to conduct $CO_2$ removal on a vast scale while the rotor blades are rotating from the tubular steel towers, the product of $CO_2$ sequestration in the air is natural carbon mineralization. Peridotite carbon mineralization based activated carbon filters ionic surfactants of water from polluted rivers and seas and kill most bacteria. Using water turbine that capture ionic surfactants of polluted rivers and seas that uses peridotite carbon mineralization based activated carbon for purification solved the problem in the water pollution of rivers and seas.

As stated in Precipitation by Harrison et al., 2013—

"Mineralization occurs naturally during weathering of silicate materials (e.g. olivine, serpentine, and wollastonite and rocks rich in CA and Mg, particularly peridotite which composes Earth's upper mantle and basaltic lava formed by partial melting of the upper mantle."

The carbon mineralization mantle peridotite is the peridotite carbon mineralization based is then the based activated carbon for purification and filters the water of polluted rivers and seas.

BRIEF SUMMARY OF THE INVENTION

It is an object of the present invention to provide a solution to the global warming caused by the effect of greenhouse gas concentration that's warming the planet. Ionization of surfactants adsorb in the interfaces, from the water-insoluble hydrophobic group that extends out of the water in the air such as methane gas adds to the greenhouse gas concentration in the atmosphere.

It is an object of the present invention to clean, purify, and disinfect (sterilize) the water of polluted rivers and seas around the globe. Sanitary, germ-free or uninfected rivers and seas are the expectations after the sterilization of these said body of waters such as rivers and seas.

Specifically, the inventor's idea of water turbine that capture surfactants of water from polluted rivers and seas that uses mantle peridotite carbon mineralization based activated carbon for purification and filtration was derived from the inventor's idea of $CO_2$ capture in air by using the rotor wind turbine blades with attached materials (peridotite) that would capture the carbon dioxide in air while the blades are rotating powers by the wind (was discovered and patterned from the chlorophyll pigment of the plant's leaves).

The rotor wind turbine blades with materials would be available to conduct $CO_2$ removal in a vast scale and the product of $CO_2$ sequestration is natural carbon. The carbon mineralization in the peridotite carbon mineralization based is then the based activated carbon for purification and filtering of water from the polluted rivers and seas.

As stated in Carbon Nanotubes (CNTS)—

"A stainless steel mesh with micro-scale pores. FIG. 5 the nanotube filter was able to separate diesel and water layers. Majumber et al., reported the transport properties through an aligned multiwalled CNT membrane structure impermeable PS matrix, consisting of substantially dense (~109-10 tubes/cm2), with ~7 nm pore diameter. The liquid flow through the noninteracting hydrophilic CNT cores was formed to be 1000-10,000 times faster than liquid transport from conventional no-slip hydrodynamic predictions."

As stated in "The Use of Nanoparticles in Polymeric and Ceramic Membrane Structures: Review of Manufacturing Procedures and Performance Improvement For Water Treatment" by Jeonghwan Kin, Bart Van der Bruggen—

"Membrane separations are powerful tools for various applications, including wastewater treatment and the removal of contaminants from drinking water. The performance of membranes is mainly limited by materials properties. Recently, successful attempts have been made to add nanoparticles or nanotubes to polymers in membrane synthesis, with particles sizes ranging from 4 nm up to 100 nm. Ceramic membranes have been fabricated with catalytic nanoparticles for synergistic effects on the membrane performance. Breakthrough affects that have been reported in the field of water and waste water treatment include fouling mitigation, improvement of permeate quality and flux enhancement. Nanometers that have been used include titania, alumina, silver, and many others. This paper reviews the role of engineered nanomaterials in (pressure driven) membrane technology for water treatment, to be applied in drinking water production and wastewater recycling. Benefits and drawbacks are described, which should be taken into account in further studies on potential risks relates to release of nanoparticles into the environment."

As stated in Environmental Pollution, July 2010 Pages 2350-2358, "Determination of Four Fluoroquinolone Antibiotics in Tap Water in Guangzhou and Macao" by Yiruhan, Jiawei Yu, et al.—

"Four fluoroquinolone antibiotics (nofloxacin, ciprofloxacin, lomefloxacin, and ennofloxacin) in tap water in Guanzhou and Macao were analyzed using high performance liquid chromatography fluorescence detection. The results showed that all target antibiotics were detected in high rate both in Guangzhou (77-5%) and Macao. In addition, the effort of rainfall on concentration of fluoroquinole antibiotics in South China was also investigated. Our result indicates that the antibiotic concentration in tap water in Guanzhou tends to obviously reduce at the beginning of rainy season, even decreases below the limit of quantification immediately. Thus, it was clarified that the heavy rain in South China has the function of reducing the fluoroquinolone antibiotics concentrations in tap water."

As stated in "Unique Metabolites Protect Earthworms Against Plant Polyphenols" by Manuel Liebelle, Nicole Strillmater, et al.

"All higher plants produce polyphenols, for defense against above-ground herbivory. These polyphenols also influences the soil micro- and macro-fauna that break down plant leaf litter. Polyphenols therefore-indirectly affect the fluxes of soil nutrients and, ultimately, carbon turnover, and ecosystem functioning in soils. It is unknown how earthwork major component of animal biomass in many soils, cope with high-polyphenols diets. Here we show that earthworms possesses a class of unique surface-active metabolites in their gut, which we term "drilodefensin." These compounds counteract the inhibitory effects of polyphenols on earthwork gut enzymes, and high polyphenol diets increase drilodefensin concentrations in both laboratory and field populations. This shows that drilodefensins protect earthworm from the harmful effects of ingested polyphenols. We have identified the key mechanism for adaptation to a dietary challenge in an animal group that has a major role in organic matter recycling in soils worldwide."

As stated in "Do You Add Sulfuric Acid to Water or Vice Versa by Anne Marie Helmenstine, PH.D. Aug. 17, 2019—

"Sulfuric acid ($H_2SO_4$) reacts very vigorously with water in a highly exothermic reaction. If you add water to concentrated sulfuric acid, it can boil and spit and you may get a nasty acid burns. If you're wondering about the temperature change, mixing 100 ml of water initially at 19 degrees C. reaches a temperature over 131 degrees C. within a minute."

Surfactants are classified into anionic (sulfonate, sulfate and phosphate esters, carboxylates); cationic head group (pH-dependent primary, secondary or tertiary amines); zwitterionic surfactants (amine); non-ionic surfactants ethoxylates; amine oxides; sulfoxides; phosphine oxides. In the case of ionic surfactants, the counter ion can be: inorganic/monatomic:

1) c cations: metals; alkali metal, alkaline earth metal, transition metal
2) anions: halides; chloride, bromide, iodide
Polyatomic/Organic
1) cations: ammonium, pyridiumium, triethanoloamine (TEA)
2) Anions: tosyls, trifluoromethalsulfonates, methylsulfate In human, pulmonary surfactant is produced in lungs in order to facilitate breathing by increasing total lung capacity, TLC, and lung compliance. As stated, surfactants are routinely deposited in numerous ways on land and into water systems whether as part of an intended process or as an individual and household waste. For example, perfluorooctane sulfonic acid (PFOS) is a persistent organic pollutant judged by the Stockholm Convention. The two major surfactants used in year 2000 were linear alkylbenezene sulfonates (LAS) and alkyl phenol ethoylates (APE). *Reference: Wikipedia.org As stated in 'Earth's Energy Budge—

"Received radiation is unevenly distributed over the planet because the sun heats equatorial regions more than the polar regions. The atmosphere and ocean work non-stop to even out solar heating imbalances through evaporation of surface water, convection, rainfall, winds, and ocean circulation. Earth is very close to being in radiative equilibrium, the situation where the incoming solar energy is balanced by an equal flow of heat to space; under that condition, global temperatures will be relatively stable. Globally, over the course of the year, the earth system-land surfaces, ocean, atmosphere absorbs and then radiates back to spare an average of about 340 watts of solar power per square meter. Anything that increases or decreases, the amount of incoming or out-going energy will change global temperature in response.

When greenhouse gas molecules absorb thermal infrared energy their temperature rises. Those gases then radiate an increased amount of thermal infrared energy, their temperature rises. Those gases then radiate an increased amount of thermal infrared energy in all directions. Heat radiated upward continues to encounter greenhouse gas molecules; those molecules also absorb the heat, and their temperature rises and the amount of heat they radiate increases. The atmosphere thins with altitude, and at roughly 5-6 kilometers, the concentration of greenhouse gases in the overlying atmosphere is so thin that heat can escape to space. Because greenhouse gas molecules radiate infrared energy in all directions, some of its spreads downward and ultimately returns to the Earth's surface temperature is thus higher than it would be if it were heated only be direct solar heating. This supplemental heating is the natural greenhouse effect.

As stated in "Melting Iceberg Alter The Oceans" by C. Clairborne Ray—

"Melting iceberg alter the oceans salinity of the oceans as iceberg melt while the sea ice is frozen salt water, iceberg are pieces of glaciers, formed of compacted snowfall, and are therefore fresh water, Melting glaciers and icebergs release fresh water and reduce the salinity of the surrounding sea. The seawater also becomes less dense changing patterns of ocean currents. The combination of factors along with atmospheric change, is partly why some oceans, including most of the North Atlantic, are becoming saltier despite increased glacial melting. Melting ice changes the ocean water chemistry in other ways, notably adding nutrients like iron and nitrates, which can feed the growth of phytoplankton, a key food for birds and fish. In conjunction with other processes, the added fresh water also increases acidity in the ocean which can adversely affect sea life. The meltwater holds lower levels of carbonate minerals shellfish use to build their shells."

As stated in https: ocean explorer.noaa.gov/facts:

"Ocean currents act much like a conveyor belt, transporting warm water and precipitation from the equator towards the poles and cold water from the poles back to the topics.

Thus, ocean currents regulate global climate, helping to counteract the uneven distribution of solar radiation reaching Earth's surface."

As stated in 'Carbon Dioxide Levels Reach The Highest Point in Human History" by Hawaii's Mauna Loa Observatory—

"The amount of carbon dioxide in earth's atmosphere has officially surpassed levels seen in the entirety of human history topping the highest point previously recorded in 80,000 years of data by more than 100 per million, or ppm. Researchers at Hawaii's Mauna Loa Observatory measured the chart-topping figure of 415 ppm-meaning carbon dioxide made up 415 of every one million gas molecules in the atmosphere.

Scientists started tracking carbon dioxide concentration at Mauna Loa in 1958. At the time, the sites carbon level hovered around 315 ppm between 2013, they had surpassed 400 ppm. Global concentrations reached this same milestone in 2015. Then, the Industrial Revolution up ended their relative stability, introducing high levels of greenhouse gases into the atmosphere as humans burned fossils fuels to support an increasingly technology-driven lifestyle. Today, global temperature stand about 1.8 degrees Fahrenheit, or 1 degree Celsius, higher than during the pre-industrial period.

As scientists in Hawaii measures carbon levels of 415 ppm, temperature in northwest Russia surged to 84 degrees Fahrenheit –30 degrees higher than the region's average high of 54 degrees, and Greenland's ice sheets continued their relentless melt season which began more than a month ahead of schedule."

Given the above statements of scientists and studies made around the world, earthworm "gut surface" has unique metabolites called drilodefensin that protect its gut from polyphenols. Unique metabolites not present in the rivers and seas that protect against ionic surfactants caused by environmental pollution nor have the compound that counteract the inhibitory effect of surfactants and cope with it.

The radiant from the atmosphere is the cause of melting of glaciers and icebergs in Greenland that release fresh water and reduce the salinity of the surrounding sea because the carbon dioxide levels in the atmosphere reached the highest point in human history. There is a huge pH imbalance of this duo (atmospheric and oceanic) that requires action on two fronts: removing more $CO_2$ out of the atmosphere and removal of surfactants out of the oceans because carbon dioxide emissions are climate altering gas.

Countries and oceans with heavy CO2 in their atmosphere located at 60° W are Yucatan, Mexico; Honduras; Costa Rica; Nicaragua; Belize; Panama; Venezuela; Columbia; Ecuador; Brazil; Guyana; Suriname; Cayenne. Oceans with heavy $CO_2$ in their atmosphere located at 25° S; 180° W; 120° W; 60° W. Heavy CO2 also noted at the atmosphere at 50° N, 25° N are Mexico City, Mexico; Guadalajara, Los Angeles, Calif. Heavy CO2 above the oceans located at 25° S, 180° W, 120° W, 60° W.

Scattered CO2 at the atmosphere of the oceans located at 250° S, 50° S of South Pacific Ocean. In the countries such as Cuba, Jamaica, Haiti, Dominican Republic.

Scattered CO2 in the atmosphere at 50° N longitude of North Atlantic. Heavy $CO_2$ in the atmosphere of Central African Republic Ethiopia, Somalia, Kenya, Sudan, Chad, Niger. Slight $CO_2$ scattered in the atmosphere of countries like Tanzania, Swaziland, Namibia, Angola, Zambia, Durban and at 50° S.

Severe/heavy $CO_2$ at the atmosphere of countries such as Sumatra, Thailand, Malaysia, Brunei, Bangkok, Cambodia, Laos, Vietnam, Myanmar, Taiwan, Philippines, Hong Kong, Tokyo Japan, Seoul Korea, North Korea. Heavy $CO_2$ in the atmosphere of 10° North Pacific Japan Sea.

Heavy $CO_2$ located at 40° N atmosphere of China in the cities of Beijing, Shanghai, Chongqing, Zhangjiakou, Changchum, Shenyang. Scattered $CO_2$ in the atmosphere of countries such as Canada, Russia, Greenland, Netherland, UK and other parts of Europe. Heavy $CO_2$ at the atmosphere of France, and Germany. Scattered $CO_2$ or slight in the atmosphere of Saudi Arabia, Kuwait, Iran, India, Pakistan, Kazakhstan, and Turkey.

DETAILED DESCRIPTION OF THE DRAWINGS

DETAILED DESCRIPTION OF THE INVENTION

Figure 1:
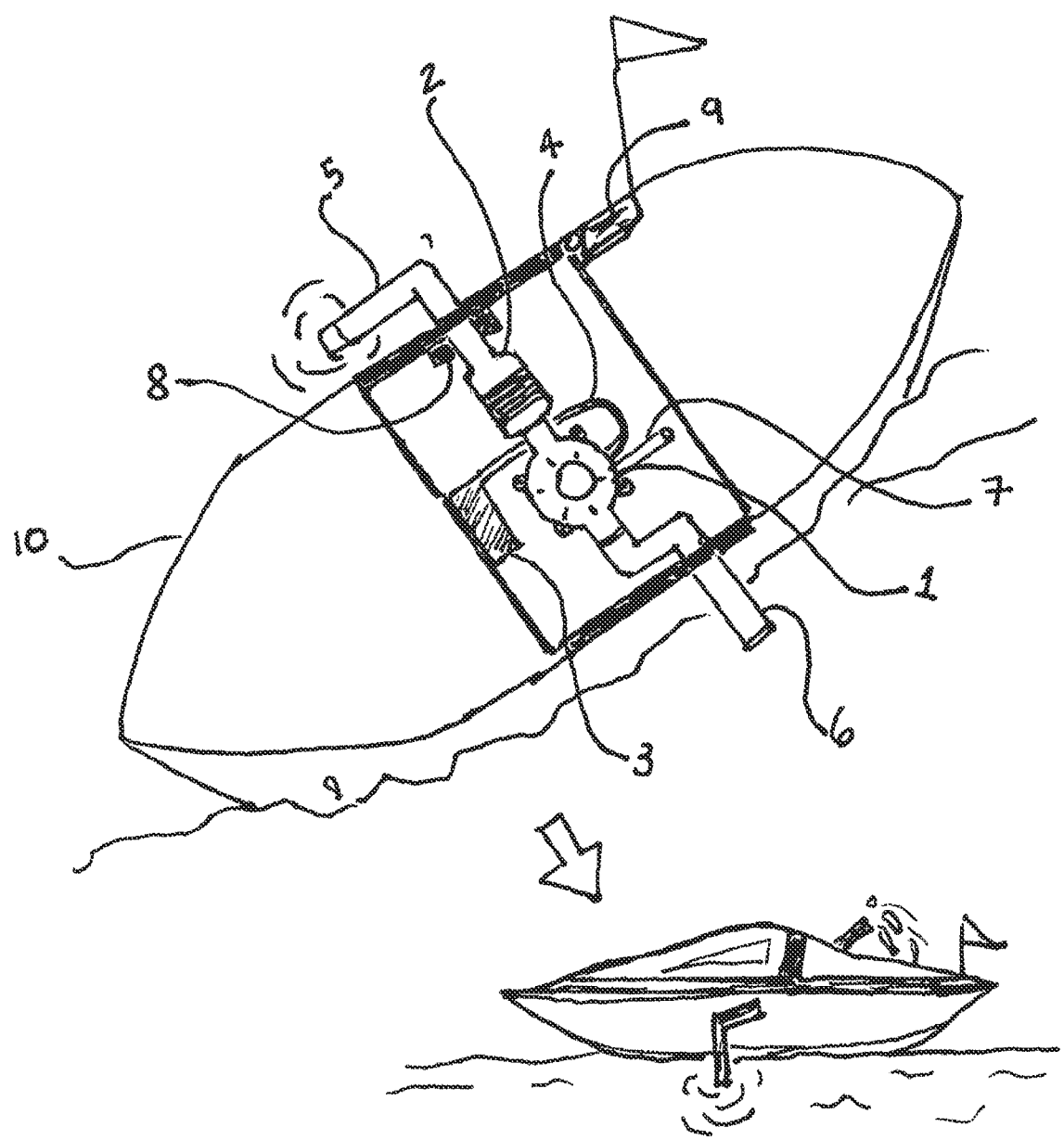
FIG. 1 is a pictorial illustration of a mini boat with activated carbon filters to treat polluted water.
Figure 2:
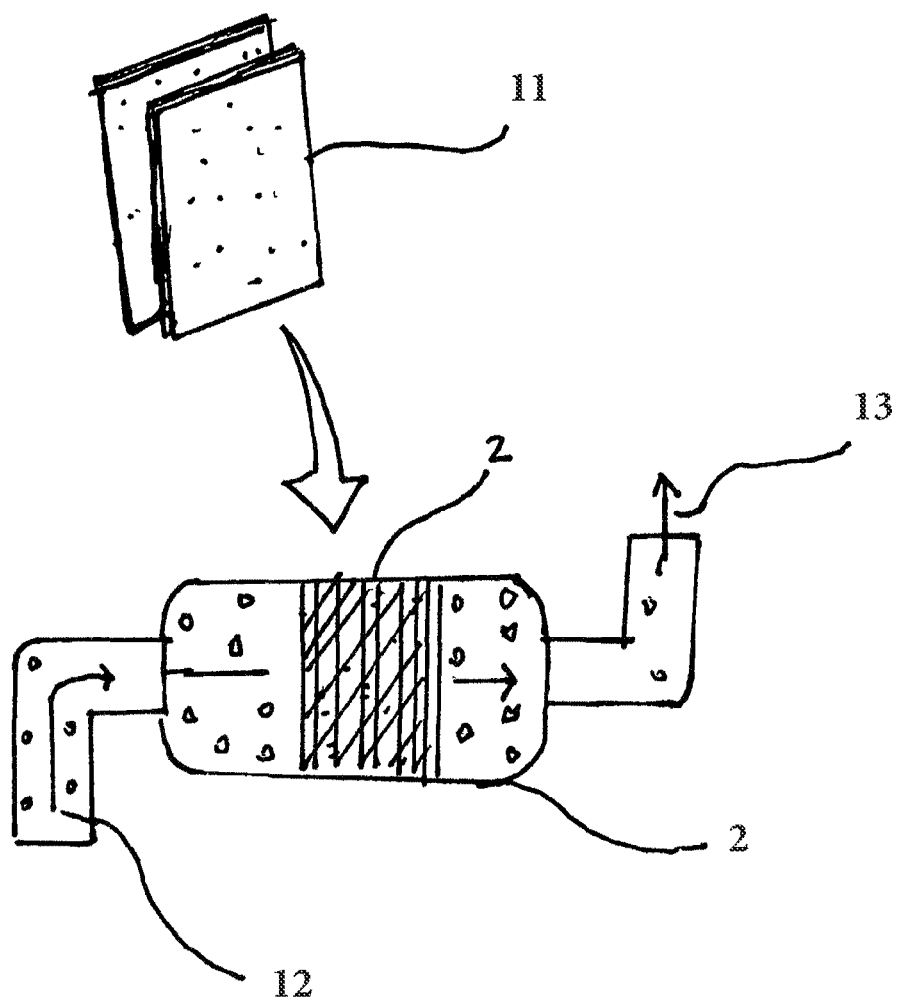
FIG. 2 is a pictorial illustration of carbon pads in an activated carbon filter being used to convert contaminated water to treated water.
Figure 3:
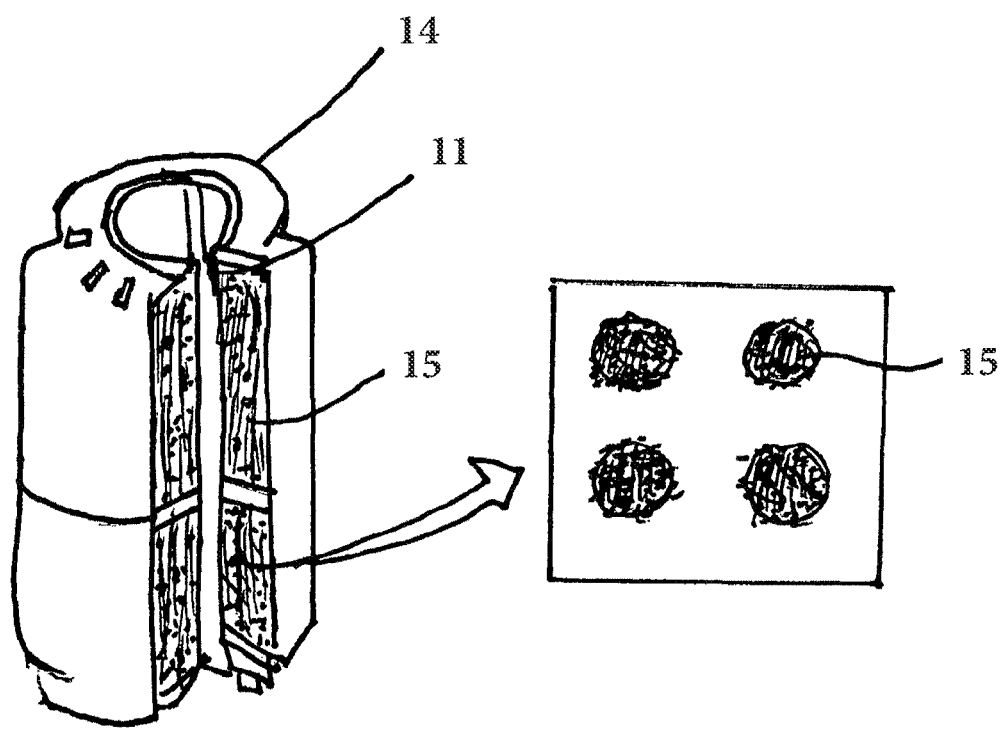
FIG. 3 is a pictorial illustration of a filter pad with mantle peridotite carbon mineralization based activated carbon and a seal.
Figure 4:
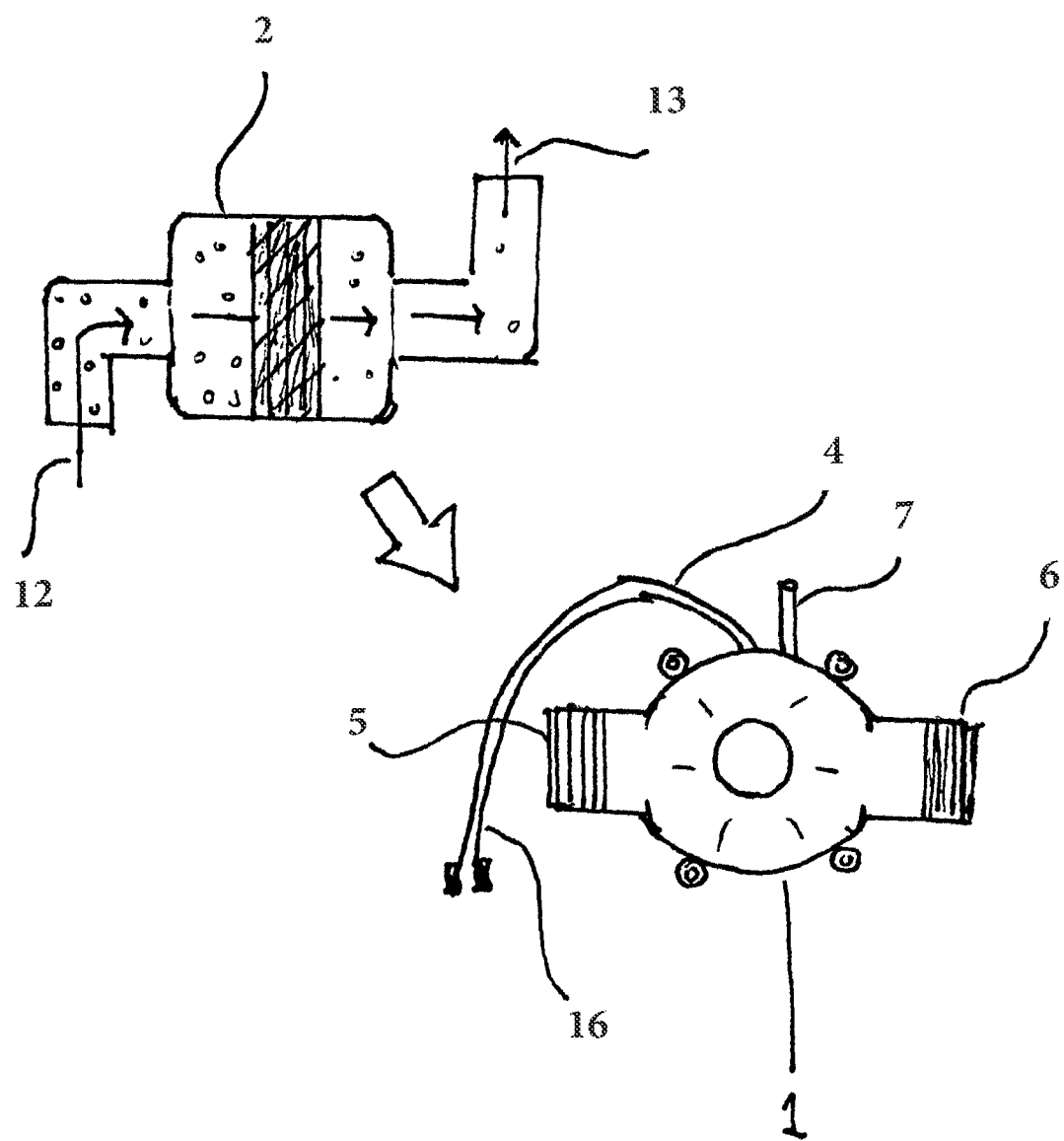
FIG. 4 is a pictorial illustration of a water turbine having activated carbon water filters treat water that moves from the water inlet of the water turbine to the water outlet.

FIG. 1
1—Turbine
(Water turbine generator)
2—Activated carbon filter
3—Rechargeable battery
4—Pos. & neg. power wires
5—Water inlet
6—Water outlet
7—Vertical shaft (for $H_2O$ refill in turbine)
8—Powerhead
9—Controller (mini-boat)
10—Mini boat
FIG. 2
2—Activated carbon water filter
11—Carbon pads
12—Contaminated water
13—Treated water
FIG. 3
14—Seal
11—Filter pad
15—Mantle peridotite carbon mineralization based activated carbon
FIG. 4
1—Turbine
6—Water outlet
5—Water inlet
16—Plastic connector
4—Pos. &. Neg. power wires
2—Activated carbon water filter
12—Contaminated water ($H_2O$)
13—Treated water ($H_2O$)
7—Vertical shaft
FIG. 5
18—Drone
10—Mini boat with portable small water turbine A portable small water turbine 1 as shown in FIG. 1 and FIG. 4 with activated carbon water filter 2 that has material available to conduct the removal of the ionic surfactants of the polluted water from seas and rivers. The inlet 5 as shown in FIG. 1 and FIG. 4 of the small water turbine 1 is attached to the pipe of the activated carbon water filter 2. As the liquid (as shown in FIG. 2) flows through the activated carbon pad 11 as shown in FIG. 2 after the water turbine 1 starts operating, the carbon pad 11 captures the ionic surfactants of the contaminated water 12 as shown in FIG. 2 and FIG. 4 and filters the water free from impurities (e.g., treated water 13 as shown in FIG. 2 and FIG. 4).

The activated carbon pad 11 as shown in FIG. 2 that is placed inside and in the middle of the activated carbon water filter tube is composed of mantle peridotite carbon mineralization based activated carbon 15 as shown in FIG. 3. The mantle peridotite carbon mineralization 15 is the product of $CO_2$ sequestration in the air by using the peridotite highly reactive rock fragments in the conduction of $CO_2$ removal on a vast scale in the air using the rotor tower blades rotating from the tubular towers.

The pipe of the activated carbon water filter is connected to the water inlet 5 as shown in FIG. 1 and FIG. 4 of the small water turbine 1 generator. After the water treatment, it passes through to the inlet 5 then to the rotating turbine blades and afterwards out to the water outlet tube 6. The water turbine generator is powered by a rechargeable battery, 100% cordless. The portable small water turbine 1 with activated carbon water filter 2 can be equipped with radar devices readable via USB or SD card built IDDA Power ¼"-20 thread to 6 AA batteries. The working mode can be online or SD card offline.

A task scheduler application is set up or installed in the computer for basic tasks such as 1) start 2) action 3) finish. To enable to run the appliance, the application is also installed to the portable small water turbine 1 with activated carbon water filter 2 as shown in FIG. 1 and FIG. 2 to control the appliance from the PC or Iphone. The PC and appliance connect with the same WIFI connection or network connection. A SIM card is placed in the slot of the appliance to connect it to the computer to mirror history of run time, cleaning hours and area cleaned in sq.ft.

Figure 5:
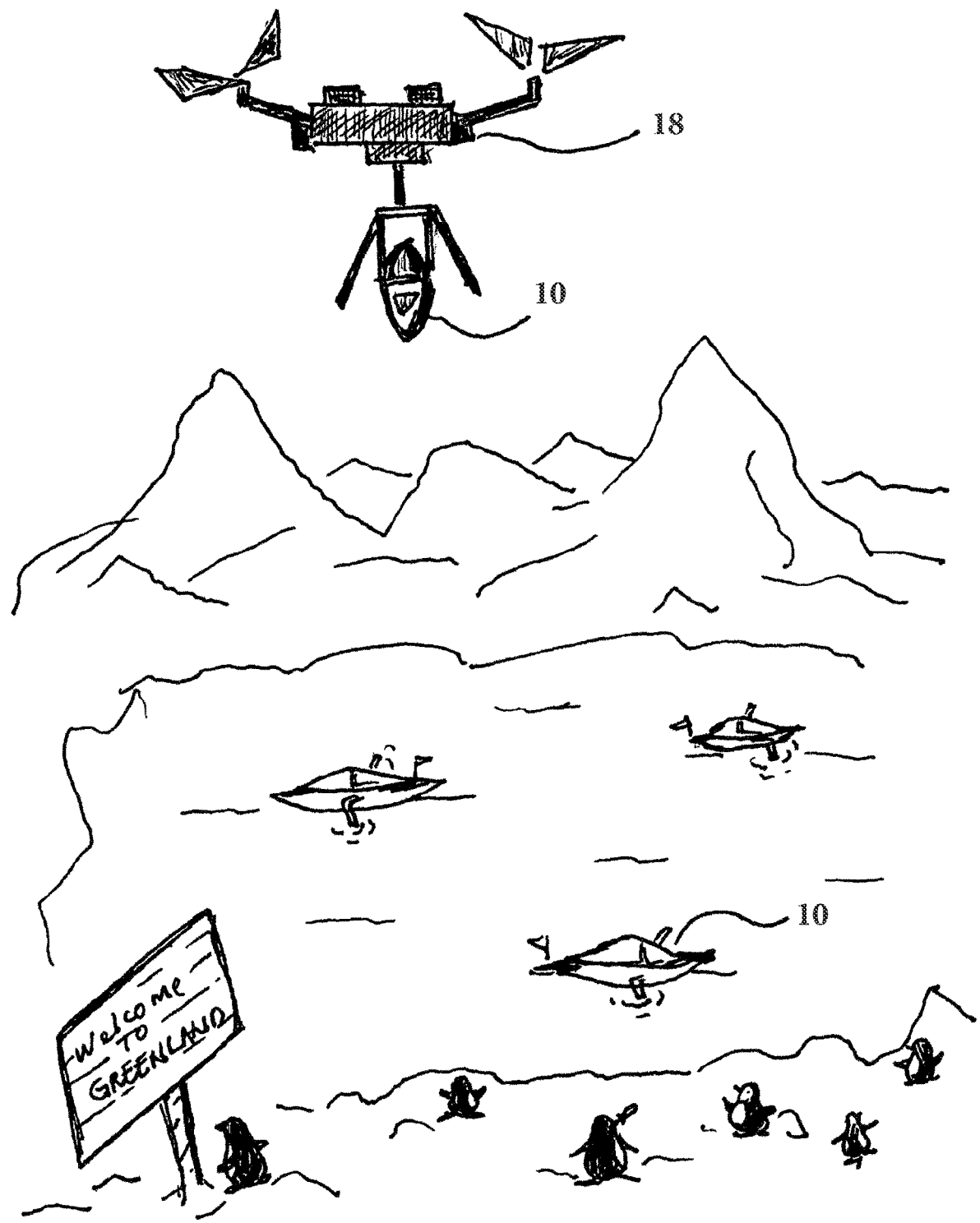
FIG. 5 is a pictorial illustration of a drone being used to drop off the mini boat having the mantle peridotite carbon mineralization based activated carbon filters

The portable small water turbine 1 with activated carbon water filter 2 is fitted and placed inside the mini boat 10 as shown in FIG. 1 and FIG. 5. FIG. 5 also shows a drone 18 being used to drop off the mini boat 10 in the contaminated river or sea. The mini boat 10 has a controller 9 as shown in FIG. 1 that uses WIFI for controlling through a tablet or mobile application. The mini boat 10 is powered by rechargeable battery.

What is claimed:

1. A method of treating polluted water using a portable mini-boat and an activated carbon water filter, comprising:
    placing the portable mini-boat in the polluted water, wherein the portable mini-boat comprises a water turbine having a water inlet and a water outlet, and an activated carbon water filter, wherein the activated carbon water filter comprises one or more carbon pads, wherein the one or more carbon pads comprise mantle peridotite carbon mineralization based activated carbon;
    activating the water turbine to begin operating such that the polluted water flows through the water inlet of the water turbine;
    flowing the polluted water through the activated carbon water filter that comprises the one or more carbon pads that comprises the mantle peridotite carbon mineralization based activated carbon, wherein the one or more carbon pads capture ionic surfactants of the polluted water, wherein the ionic surfactants are collected from a surface of the polluted water; and
    flowing treated water through the water outlet of the activated carbon water filter.

2. The method of claim 1, further comprising, dropping the portable mini-boat into the polluted water.

3. The method of claim 1, further comprising, operating the portable mini-boat using remote control.

4. The method of claim 1, wherein the polluted water comprises rivers and seas.

5. The method of claim 1, wherein the portable mini-boat is movable over the polluted water and is not restricted in movement over the polluted water.

* * * * *